United States Patent [19]
Elion et al.

[11] 3,970,659
[45] July 20, 1976

[54] PREPARATION OF CYANOPYRIDINES

[75] Inventors: Glenn R. Elion, Avenel; Arthur E. Klink, Lebanon, both of N.J.

[73] Assignee: Merck & Co., Inc., Rahway, N.J.

[22] Filed: Nov. 18, 1975

[21] Appl. No.: 632,935

[52] U.S. Cl. ............................................ 260/294.9
[51] Int. Cl.$^2$ ........................................ C07D 213/57
[58] Field of Search .................... 260/294.9, 465 C

[56] References Cited
UNITED STATES PATENTS

| | | | |
|---|---|---|---|
| 2,510,605 | 6/1950 | Porter et al. ...................... | 260/294.9 |
| 2,833,807 | 5/1958 | Farkas et al. .................... | 260/465 C |
| 2,839,535 | 6/1958 | Hadley et al. ..................... | 260/294.9 |
| 2,861,999 | 11/1958 | D'Alessandro ................... | 260/294.9 |
| 3,297,587 | 1/1967 | Scherhag et al. .................. | 252/432 |
| 3,544,617 | 12/1970 | Oga et al. ......................... | 260/465 C |
| 3,868,400 | 2/1975 | Norton .............................. | 260/464 |
| 3,901,933 | 8/1975 | Norton ............................. | 260/465 C |

FOREIGN PATENTS OR APPLICATIONS 2,435,134  11/1973  Germany ......................... 260/294.9

*Primary Examiner*—Alan L. Rotman
*Attorney, Agent, or Firm*—Richard A. Thompson; J. Jerome Behan

[57] ABSTRACT

Cyanopyridines are prepared by bringing a reactant stream comprising an alkyl substituted pyridine, ammonia, steam and oxygen into contact with a novel catalyst composition which results in high selectivity to the desired cyanopyridine.

5 Claims, No Drawings

PREPARATION OF CYANOPYRIDINES

This invention relates to chemical compositions and a process for the production of cyanopyridines from alkyl substituted pyridines.

One of the problems inherent in an ammoxidation system and particularly in a system employing excess oxygen in the reactant stream is undesirable combustion of organic reactant and ammonia to unwanted by-products rather than nitrile products. This, of course, adds to process costs in that more reagent is required to produce a given amount of nitrile (e.g., yields are reduced) and also larger capital investment is required to build a plant for a given capacity. Obviously then, a reduction in the undesired combustion of ammonia and organic reactant with the attendant yield increase is a desirable objective.

It has now been found that in the vapor phase ammoxidation of alkyl substituted pyridines the yield of desired cyanopyridine can be significantly increased and ammonia and hydrocarbon decomposition mitigated, and this is accomplished in accord with this invention by utilizing the inventive catalyst compositions in a fixed bed catalyst system.

An advantage of the present invention is that the catalyst does not have to be periodically regenerated and still the high selectivity to the desired cyanopyridine remains. Another advantage is that an adiabatic or isothermal type reactor can be utilized which results in allowance of temperature fluctuations without any significant decrease in the high selectivity to the desired cyanopyridine by utilizing the catalyst compositions of the present invention. Also, low molar ratio of ammonia and oxygen to the alkyl substituted pyridine can be utilized which results in lower amounts of undesirable side products.

An important aspect of the present invention is the high selectivity to the desired cyanopyridine. That is, of the alkyl substituted pyridine that is converted into products by coming into contact with the catalyst, a higher percentage is converted to the desired 3-cyanopyridine than is shown in the prior art.

Thus, according to the invention, there is described a process for the production of cyanopyridines from alkyl pyridines which comprises passing as a reactant stream a gaseous mixture comprising:
1. an alkyl substituted pyridine;
2. ammonia;
3. steam; and
4. oxygen wherein the mole ratios of said reactants are:
  ammonia:alkyl pyridine, 1:1 to 10:1;
  steam:alkyl pyridine, 0.01:1 to 10:1;
  oxygen:alkyl pyridine, 2:1 to 50:1;

the improvement being passing said reactant stream over a fixed bed ammoxidation catalyst at a temperature of about 280° to 400°C. and wherein said catalyst consists essentially of $(V_2O_5+MoO_3+P_2O_5)/(TiO_2+Al_2O_3)$ in a molar ratio of 2.5:1.0:0.01/21.8:5.7.

The catalyst composition utilized in carrying out the process of the present invention is a novel and useful composition. The precise molar ratios of the catalyst components account for the unusual and novel results.

The novel composition consists of vanadium pentoxide ($V_2O_5$), molybdenum oxide ($MoO_3$), and phosphorus pentoxide ($P_2O_5$) on titanium dioxide ($TiO_2$) and alumina ($Al_2O_3$) wherein the molar ratios of ($V_2O_5$:$MoO_3$:$P_2O_5$)/($TiO_2$:$Al_2O_3$) are 2.5:1.0:0.01/21.8:5.7.

In carrying out the process of the invention, the reactor and attendant equipment is prepared in the usual way, the reactor being charged with catalyst and otherwise prepared for startup including the conditioning of catalyst, if desired. The alkyl substituted pyridine, ammonia, steam and oxygen stream are then passed over the catalyst at reaction conditions at certain mole percent ratios. Preferred reaction temperature is about 325° to about 355°C. at essentially atmospheric pressure.

By the term "high selectivity" is meant that the amount of alkyl pyridine converted to the cyanopyridine is greater than 70%.

Typical alkyl substituted pyridines suitable for conversion into cyanopyridines according to this invention are 2-, 3- and 4-picolines; the 2,3-, 2,4-, 2,5-, 2,6- and 3,4-dimethyl pyridines; the 2,3,4-, 2,4,6-, 236- and 2,3,5-trimethyl pyridines; the 2-, 3- and 4-ethyl pyridines; 2-methyl-5-ethyl pyridine, and 2-ethyl-5-methyl pyridine.

The catalyst support suitable for this invention is specific in order to achieve the catalyst activity and catalyst selectivity to the desired product. In this particular invention, the catalyst support is $TiO_2 + Al_2O_3$.

The weight percent loading of the catalyst on the support can vary from about 5 to 50%. A more preferred weight percent utilized in the practice of this invention is from about 25 to 30%.

EXAMPLE 1

Preparation of catalyst $(V_2O_5+MoO_3+P_2O_5)/(TiO_2 + Al_2O_3)$

To 350 ml. of 12N hydrochloric acid (HCl) is added 50.04 gm. of ammonium metavanadate ($NH_4VO_3$) and the mixture heated to 40°C. Then 15.21 gm. of ammonium paramolybdate $[(NH_4)_6Mo_7O_{24} \cdot 4H_2O]$ is added to the solution with continued heating to about 80°C. To the heated solution is added 0.23 gm. of phosphoric acid ($H_3PO_4$ - 85%) followed by 50.0 gm. of gamma-alumina ($\gamma Al_2O_3$) with continuous stirring. The length of heating time is not critical. Then 150.0 gm. of titanium dioxide ($TiO_2$) submicron powder is added to the mixture with continuous stirring until the mixture is very viscous. The mixture is vacuum dried and calcined in air at 450°C. for 16 hours.

EXAMPLE 2

The catalyst prepared in Example 1 is used to prepare cyanopyridines in an isothermal reactor as follows: Two cubic centimeters (2 cc.) of the catalyst prepared in Example 1 is placed into a 1/4 inch (0.635 centimeter) I.D. stainless stell isothermal reactor and connected to a gas chromatograph apparatus in order to analyze the feed and product compositions of the reactor. The feed composition is adjusted to enter the reactor as 1.0% 3-picoline, 2.0% ammonia ($NH_3$), 4.0% steam ($H_2O$) and the remainder as air giving 22.2% oxygen. The contact time of the reactants in the reactor is about 4.7 seconds. At a temperature of about 337°C., the conversion of 3-picoline is about 52.0% and the selectivity of 3-cyanopyridine is about 81.0%.

EXAMPLE 3

The catalyst prepared in Example 1 is used to prepare cyanopyridines in an isothermal reactor as follows: 2 cc. of the catalyst prepared in Example 1 is placed into a 1/4 inch (0.635 centimeter) I.D. stainless steel isothermal reactor and connected to a gas chromatograph apparatus in order to analyze the feed and product compositions of the reactor. The feed composition is adjusted to enter the reactor as 1.0% 2-methyl-5-ethyl pyridine, 2.0% ammonia ($NH_3$), 4.0% steam ($H_2O$) and the remainder as air giving 22.2% oxygen. The contact time of the reactants in the reactor is about 4.7 seconds. At a temperature of about 350°C., the conversion of 2-methyl-5-ethyl pyridine is about 23.0% and the selectivity to 3-cyanopyridine is about 74.0%.

What is claimed is:

1. A process for the production of cyanopyridines from alkyl pyridines which comprises passing as a reactant stream a gaseous mixture comprising:
   1. an alkyl substituted pyridine;
   2. ammonia;
   3. steam; and
   4. oxygen wherein the mole ratios of said reactants are:
   ammonia:alkyl pyridine, 1:1 to 10:1;
   steam:alkyl pyridine, 0.01:1 to 10:1;
   oxygen:alkyl pyridine, 2:1 to 50:1;

the improvement being passing said reactant stream over a fixed bed ammoxidation catalyst at a temperature of about 280° to 400°C. and wherein said catalyst consists essentially of ($V_2O_5$+$MoO_3$+$P_2O_5$)/($TiO_2$+$Al_2O_3$) in a molar ratio of 2.5:1.0:0.01/21.8:5.7.

2. A catalyst composition consisting essentially of ($V_2O_5$+$MoO_3$+$P_2O_5$)/($TiO_2$+$Al_2O_3$) wherein the molar ratios of $V_2O_5$:$MoO_3$:$P_2O_5$/$TiO_2$:$Al_2O_3$ are 2.5:1.0:0.01/21.8:5.7.

3. The process according to claim 1 wherein the alkyl substituted pyridine is selected from the group consisting of 2-picoline, 3-picoline, 4-picoline and 2-methyl-5-ethyl pyridine.

4. The process according to claim 1 wherein the alkyl substituted pyridine is 3-picoline.

5. The process according to claim 1 wherein the alkyl substituted pyridine is 2-methyl-5-ethyl-pyridine.

* * * * *